US008022200B2

(12) United States Patent
Wershofen et al.

(10) Patent No.: US 8,022,200 B2
(45) Date of Patent: Sep. 20, 2011

(54) PROCESS FOR THE PREPARATION OF LIQUID, STORAGE-STABLE ORGANIC ISOCYANATES OF LOW COLOR NUMBER CONTAINING CARBODIIMIDE AND/OR URETONIMINE GROUPS

(75) Inventors: Stefan Wershofen, Mönchengladbach (DE); Manfred Schmidt, Dormagen (DE); Hans-Georg Pirkl, Leverkusen (DE); Nobuhiro Kamiyama, Hyogo (JP); Shinichi Murakami, Hyogo (JP); Tetsuo Harada, Hyogo (JP)

(73) Assignee: Bayer MaterialScience AG, Leverkusen (DE)

( * ) Notice: Subject to any disclaimer, the term of this patent is extended or adjusted under 35 U.S.C. 154(b) by 1767 days.

(21) Appl. No.: 11/173,482

(22) Filed: Jul. 1, 2005

(65) Prior Publication Data
US 2006/0025557 A1 Feb. 2, 2006

(30) Foreign Application Priority Data

Jul. 13, 2004 (DE) .......................... 10 2004 033 849

(51) Int. Cl.
*C07C 267/00* (2006.01)
*C07D 229/00* (2006.01)
(52) U.S. Cl. ................ 540/202; 252/182.2; 252/182.21; 252/182.22; 252/182.29; 528/44; 528/67; 528/73; 528/76; 528/80; 528/85; 548/951; 548/952; 560/330; 560/334; 560/336
(58) Field of Classification Search ............... 252/182.2, 252/182.21, 182.22, 182.29; 528/44, 67, 528/73, 76, 80, 85; 540/202; 548/952, 951; 560/25, 26, 330, 115, 158, 331, 332, 333, 560/334, 336
See application file for complete search history.

(56) References Cited

U.S. PATENT DOCUMENTS

| 2,853,473 | A | | 9/1958 | Campbell at al |
| 4,088,665 | A | | 5/1978 | Findeisen et al. |
| 4,120,884 | A | * | 10/1978 | Woerner et al. ............... 560/331 |
| 4,260,554 | A | * | 4/1981 | Ohlinger et al. ............... 560/331 |
| 5,202,358 | A | | 4/1993 | Scholl et al. .................. 521/160 |
| 5,354,888 | A | | 10/1994 | Scholl ........................... 564/252 |
| 5,610,408 | A | * | 3/1997 | Imokawa et al. .......... 252/182.2 |
| 6,120,699 | A | | 9/2000 | Narayan et al. ............ 252/182.2 |
| 7,030,274 | B2 | * | 4/2006 | Rosthauser et al. .......... 564/252 |

* cited by examiner

*Primary Examiner* — Rabon Sergent
(74) *Attorney, Agent, or Firm* — N. Denise Brown; Noland J. Cheung

(57) ABSTRACT

The invention relates to a process for the preparation of liquid, storage-stable isocyanate mixtures which are characterized by a low color number and which contain carbodiimide (CD) and/or uretonimine (UI) groups. This invention also relates to the isocyanate mixtures obtained by this process, to their use for the preparation of blends with further isocyanates, and to the preparation of prepolymers containing isocyanate groups and of polyurethane plastics, preferably polyurethane foams from these isocyanate mixtures.

10 Claims, No Drawings

PROCESS FOR THE PREPARATION OF LIQUID, STORAGE-STABLE ORGANIC ISOCYANATES OF LOW COLOR NUMBER CONTAINING CARBODIIMIDE AND/OR URETONIMINE GROUPS

CROSS REFERENCE TO RELATED PATENT APPLICATION

The present patent application claims the right of priority under 35 U.S.C. §119 (a)-(d) of German Patent Application No. 10 2004 033 849.3, filed Jul. 13, 2004.

BACKGROUND OF THE INVENTION

The invention relates to a process for the preparation of liquid, storage-stable isocyanate mixtures exhibiting a low color number and containing carbodiimide (CD) and/or uretonimine (UI) groups. This invention also relates to the isocyanate mixtures obtained by this process, to their use for the preparation of blends with other isocyanates, for the preparation of prepolymers containing isocyanate groups, and for the preparation of polyurethane plastics, preferably polyurethane foams.

Isocyanate mixtures containing CD and/or UI groups can be prepared in a simple manner using the highly active catalysts from the phospholine series, in particular catalysts of the phospholine oxide series. Suitable processes are known and described in U.S. Pat. No. 2,853,473, EP-A-515 933 and U.S. Pat. No. 6,120,699.

The high catalytic activity of the phospholine catalysts, particularly the phospholine oxide catalysts, is on the one hand desirable in order to start up the carbodiimidization reaction under gentle temperature conditions. However, on the other hand, no process is known to date which ensures the effective termination of the phospholine catalysis or phospholine oxide catalysis without limitation. The carbodiimidized isocyanates tend to after-react, i.e. they release gas as a result of $CO_2$-formation. This then leads to a build up of pressure in, for example, the storage tanks, especially when the temperature rises.

There have been numerous attempts to discover an effective means to terminate the phospholine catalysis. Suitable terminators are mentioned in, e.g., the patent specifications EP-A-515 933, EP-A-609 698 and U.S. Pat. No. 6,120,699. These include, e.g., acids, acid chlorides, chloroformates and silylated acids. Termination of the catalyst with acids, which can, for example, also be in the form of acid chlorides, is not sufficiently effective.

According to the disclosure of EP-A-515 933, CD/UI-containing isocyanate mixtures prepared by means of phospholine catalysis are terminated with at least an equimolar amount of, and preferably 1 to 2 times the molar amount of, trimethylsilyl trifluoromethanesulfonate (TMST), based on the catalyst employed. In practice, however, it has been found that CD/UI-containing isocyanates prepared in such a way are of only limited suitability for the preparation of prepolymers. Prepolymers are the reaction products of these CD/UI-containing isocyanates with polyols. The correspondingly prepared prepolymers, i.e. reaction products of polyols and the CD/UI-modified isocyanates, tend to release gas, which can lead to a build up of pressure in the transportation tanks or to foaming during handling of such products.

This problem can be avoided by employing the silylated acid used for terminating the phospholine catalyst, analogously to EP-A-515 933, in higher molar equivalents (e.g. 5:1-10:1, based on the catalyst employed). In practice, however, this results in the resultant CD/UI-modified isocyanates having a significantly poorer color number. This then also applies to the prepolymers prepared therefrom.

This also applies if the phospholine catalyst is terminated with acids of the trifluoromethanesulfonic acid type in accordance with U.S. Pat. No. 6,120,699. Prepolymers prepared therefrom also have a considerably increased color number.

The object of the present invention was to provide a process for the preparation of liquid, storage-stable isocyanate mixtures containing carbodiimide and/or uretonimine groups which does not have the deficiencies referred to above. It was also an object to prepare liquid, storage-stable isocyanate mixtures exhibiting low color numbers.

SUMMARY OF THE INVENTION

The invention relates to a process for the preparation of organic isocyanates containing carbodiimide and/or uretonimine groups. This process comprises (1) partially carbodiimidizing isocyanate groups of an organic isocyanate in the presence of one or more catalysts of the phospholine type, (2) subsequently terminating the carbodiimidization reaction by the addition of a silylated acid corresponding to the general formula:

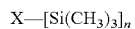

wherein:
X: represents the neutral acid radical which is obtained from an n-basic acid having a pKa value of not more than 3 by the removal of the acid hydrogen atoms, with the proviso that suitable n-basic acids exclude hydrogen halide acids,
and
n represents an integer from 1 to 3,
and (3) adding a compound selected from the group consisting of non-silylated acids, acid chlorides, sulfonic acid esters and mixtures thereof.

Silylated acids suitable for terminating the carbodiimization reaction include those corresponding to the general formula $X—[Si(CH_3)_3]_n$ in which X and n are as defined above. It is preferred that the silylated acids used are O-silylated, oxygen-containing acids which, in the non-silylated form, have a pKa value of not more than 3. These include compounds, such as, for example, trifluoromethanesulfonic acid trimethylsilyl ester (trimethylsilyl trifluoromethanesulfonate, or TMST).

The present invention also relates to the organic isocyanates containing carbodiimide and/or uretonimine groups which are prepared by the abovementioned process. These organic isocyanates containing carbodiimide and/or uretonimine groups are liquid at room temperature and, depending on the CD/UI content and/or on the isocyanate employed, may be liquid at low temperatures (e.g. 0° C.).

In accordance with the present invention, the resultant organic isocyanates containing carbodiimide and/or uretonimine groups may be blended with one or more other organic polyisocyanates to form a blend of organic polyisocyanates. In addition, these CD and/or UI containing organic isocyanates, and blends with one or more additional organic polyisocyanates, are suitable for preparing prepolymers of isocyanates, i.e. isocyanate-terminated prepolymers, which exhibit improved color number.

Finally, the present invention also relates to the preparation of polyurethanes such as, for example, foams and/or plastics, from the novel organic isocyanates containing carbodiimide and/or uretonimine groups of this invention, from blends of these novel CD and/or UI group containing isocyanates with other organic isocyanates, and from prepolymers exhibiting improved color number prepared from these novel isocyanates and blends of these with other isocyanates.

DETAILED DESCRIPTION

Any desired organic di- or poly-isocyanates can be employed as starting materials for the process according to the invention. It is preferred, however, that the carbodiimidization process according to the invention uses the organic diisocyanates, which are typically employed in polyurethane chemistry.

The following di- and poly-isocyanates are particularly suitable: aromatic diisocyanates, such as 2,4- and/or 2,6-diisocyanatotoluene (TDI); 2,2'-, 2,4'- and/or 4,4'-diisocyanatodiphenylmethane (MDI) and any desired mixtures of such aromatic diisocyanates; polyisocyanate mixtures of the diphenylmethane series having a content of monomeric diisocyanatodiphenylmethane isomers of 80 to 100 wt. % and 0 to 20 wt. % of polyisocyanates of the diphenylmethane series which are more than difunctional, in which the diisocyanatodiphenylmethane isomers comprise from 0 to 100 wt. % of 4,4'-diisocyanatodiphenyl-methane, from 0 to 100 wt. % of 2,4'-diisocyanatodiphenylmethane, and from 0 to 8 wt. % of 2,2'-diisocyanatodiphenylmethane, with the sum of the percentages by wt. of the 4,4'-, 2,4'- and 2,2'-isomers totaling 100% by wt. of the monomer; and polyphenylpolymethylene polyisocyanates, which are prepared by aniline-formaldehyde condensation and subsequent phosgenation ("crude MDI").

The carbodiimidization reaction of the process of the invention is carried out in the presence of one or more catalysts of the phospholine type. The catalysts of the phospholine type are known and described in, for example, EP-A-515 933 and U.S. Pat. No. 6,120,699, the disclosures of which are hereby incorporated by reference. Typical examples of these catalysts include, for example, the mixtures, as are known and described in the art, of the phospholine oxides which correspond to the general formulas:

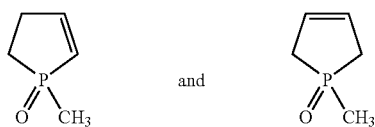

and

The amount of catalyst employed in the present invention depends on the quality of the starting isocyanates. Thus, the specific amount of catalyst needed can be easily determined by means of a simple preliminary experiment.

The carbodiimidization reaction is generally carried out in the temperature range between 50 and 150° C., and preferably from 60 to 100° C. The optimum reaction temperature obviously depends on the nature of the starting isocyanates, and this can also be readily determined in a simple preliminary experiment.

The carbodiimidization reaction is, in general, interrupted when a degree of carbodiimidization of 3 to 50%, preferably 5 to 30%, is reached. As used herein, the degree of carbodiimidization is the percentage of carbodiimidized isocyanate groups, based on the total amount of isocyanate groups present in the starting isocyanate compound.

The degree of carbodiimidization can be determined while the process according to the invention is being carried out by determination of the NCO value. The NCO content of the reaction mixture is readily determined by, e.g., means of titration, which is known per se to the person of ordinary skill in the art, or by means of any suitable online methods. Suitable online methods include, e.g., near infra-red analysis and middle infra-red analysis.

The degree of carbodiimidization can also be determined while the process according to the invention is being carried out, e.g., from the amount of carbon dioxide escaping from the reaction mixture. This amount of carbon dioxide, which can be readily determined volumetrically, provides information about the degree of carbodiimidization reached at any point in time.

Furthermore, in principle, any other offline or online methods of process monitoring known to the skilled artisan can also be employed.

To end the carbodiimidization reaction, a silylated acid which corresponds to the general formula: $X-[Si(CH_3)_3]_n$, wherein X and n have the meaning as set forth above, is employed as a terminator. Preferably at least an equimolar amount, more preferably a 1- to 5-fold molar excess, and most preferably a 1- to 3-fold molar excess, based on the molar amount of the catalyst, of a silylated acid is added as a terminator.

Suitable compounds to be used as the silylated acid include, for example, silylated sulfonic acids, such as trifluoromethanesulfonic acid trimethylsilyl ester (TMST) or methanesulfonic acid trimethylsilyl ester, or silylated esters of acids of phosphorus, such as phosphoric acid tris(trimethylsilyl ester) or phosphoric acid diethyl ester-trimethylsilyl ester.

In addition to the addition of the silylated acids as terminators, the process of the present invention requires the addition of a compound selected from the group consisting of non-silylated acids, acid derivatives of a non-silylated acid and mixtures thereof. In particular, suitable acid derivatives of a non-silylated acid include, for example, acid chlorides and/or sulfonic acid esters. These non-silylated acids and acid derivatives of non-silylated acids act as a stabilizer in the process according to the present invention. The addition of this stabilizer compound can take place either at the same time as the addition of the terminator or in a subsequent step.

Suitable non-silylated acids which can be employed in the present invention as stabilizers include, for example, optionally halogenated, aliphatic and/or cycloaliphatic and/or aromatic, mono-, di- and/or polycarboxylic acids, such as e.g. acetic acid, adipic acid, cyclohexanedicarboxylic acid, α-chloropropionic acid, benzoic acid, phthalic acid, isophthalic acid, etc., as well as sulfonic acids, HCl and/or phosphoric acids and mono- and/or diesters thereof, such as e.g., dibutyl phosphate. Suitable acid chlorides which can be employed include the acid chlorides derived from the optionally halogenated, aliphatic and/or cycloaliphatic and/or aromatic, mono-, di- and/or polycarboxylic acids or sulfonic acids, as well as carbamic acid chlorides, such as e.g., n-butylcarbamic acid chloride. Suitable sulfonic acid esters which can be employed include, e.g., p-toluenesulfonic acid methyl ester and p-toluenesulfonic acid ethyl ester.

These additional stabilizers are employed in amounts of between 100 and 1,000 ppm, preferably between 10 and 500 ppm, and most preferably between 50 and 250 ppm, based on the weight of the organic isocyanates containing carbodiimide and/or uretonimine groups.

It has been found in accordance with the present invention that the combined addition of the silylated acid with an additional stabilizer, comprising at least one non-silylated acid and/or at least one acid chloride and/or at least one sulfonic acid ester as described above, that can effectively terminate the phospholine catalysis, and at the same time, low color values can be obtained in the resultant isocyanate and in prepolymers prepared from these isocyanates. In the case of the sole addition of the silylated acid as a terminator, as described in the prior art, the phospholine catalysis can be terminated effectively only by addition of large quantities of silylated acid. However, large quantities of silylated acids lead to increased color values of the resultant isocyanates produced in this manner, mixtures of these with other isocyanates, and prepolymers prepared from these isocyanates and mixtures thereof. The same end-result occurs when a non-silylated acid, an acid chloride or a sulfonic acid ester is added solely (i.e. without the silylated acid). The presently required combined addition (either simultaneously or sequentially) of the silylated acid, with at least one non-silylated acid and/or at least one acid chloride and/or at least one sulfonic acid ester, therefore produces a synergistic effect.

Prepolymers containing isocyanate groups, i.e. isocyanate-terminated prepolymers, are obtained by reacting the organic isocyanates containing carbodiimide and/or uretonimine groups prepared by the process according to the invention, with conventional polyols which are known to be suitable in polyurethane chemistry. Suitable polyols include both simple polybasic alcohols of the molecular weight range from 62 to 599 g/mol, and preferably 62 to 300 g/mol, such as e.g. ethylene glycol, trimethylolpropane, propane-1,2-diol, butane-1,2-diol or butane-2,3-diol, hexanediol, octanediol, dodecanediol and/or octadecanediol, and preferably, higher molecular weight polyether polyols and/or polyester polyols of the type known per se from polyurethane chemistry having molecular weights from 600 to 8,000 g/mol, preferably 800 to 4,000 g/mol, and which contain at least two, typically 2 to 8, and preferably 2 to 4 primary and/or secondary hydroxyl groups. Examples of such polyols are described in, for example, U.S. Pat. No. 4,218,543, column 7, line 29 to column 9, line 32, the disclosure of which is hereby incorporated by reference.

The advantages of the process according to the invention are readily apparent.

Both the isocyanates containing carbodiimide and/or uretonimine groups, and the prepolymers prepared therefrom exhibit a good storage stability and a light color.

These organic isocyanates containing carbodiimide and/or uretonimine groups and the prepolymers prepared therefrom are valuable starting materials for the preparation of polyurethane plastics and/or foams by the isocyanate polyaddition process.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

Examples

Starting Materials:

Isocyanate A: 4,4'-diphenylmethane-diisocyanate having an NCO content: 33.6 wt. % (Desmodur 44M®, Bayer MaterialScience AG)

Catalyst A: a catalyst of the phospholine oxide type: a technical-grade mixture of 1-methyl-1-oxo-1-phosphacyclopent-2-ene and 1-methyl-1-oxo-1-phosphacyclopent-3-ene, 10% strength in toluene Terminator A: trimethylsilyl trifluoromethanesulfonate (TMST)

Polyol A: a polyether polyol of propylene oxide and ethylene oxide units having 80-90% primary OH groups, a functionality of 3, an OH number of 28 mg KOH/g and a viscosity of approx. 1,200 mPas at 25° C. (Multranol® 3901, Bayer MaterialScience LLC)

General instructions for the preparation of the organic isocyanate containing carbodiimide and/or uretonimine groups:

10 kg technical-grade Isocyanate A, i.e. 4,4'-MDI, were heated to 60° C. under $N_2$, while stirring, and 352 mg of the catalyst solution, Catalyst A, (3.5 ppm; 0.3 mmol) were added. The reaction mixture was heated at 97° C. for 240 min under $N_2$ while stirring. Thereafter, the carbodiimidization was terminated by addition of 101 mg TMST, i.e. Terminator A, (10 ppm; 0.45 mmol), and the mixture was subsequently stirred for 1 hour. In Examples 1 to 6, which are in accordance with the present invention, a stabilizer (isophthalic acid dichloride [IPDC] in Example 1; α-chloropropionic acid [α-CIPA] in Example 2; p-toluenesulfonic acid methyl ester [p-TSME] in Example 3; gaseous HCl [HCl] in the form of a masterbatch in 4,4'-MDI in example 4; sebacic acid dichloride [SDC] in example 5; dibutyl phosphate [DBP] in Example 6) was then added, in the amounts as shown in the table. In Comparison Examples 1 to 3, the addition of the additional stabilizer was omitted. However, in Comparison Example 2, the amount of TMST was increased to 55 ppm, and in Comparison Example 3, 70 ppm of trifluoro-methanesulfonic acid was employed as the terminator instead of TMST. The results are summarized in the following table.

General instructions for the preparation of a prepolymer from reacting an organic isocyanate containing carbodiimide and/or uretonimine groups with a polyol:

167 g Polyol A were added to (in each case) 500 g of the isocyanate prepared according to the above instructions, at 50° C. under $N_2$ while stirring, and the mixture was kept at 80° C. for a further 2 h under $N_2$ while stirring. The prepolymers were characterized by analysis the following day. To evaluate the stability of the prepolymers, isothermal pressure tests (12 h/90° C.) were carried out. The results are summarized in the following table.

| | | | Isocyanate | | | | Prepolymer | | Pressure test to evaluate the storage stability [bar/d] Rate of increase |
|---|---|---|---|---|---|---|---|---|---|
| | TMST [ppm] | Stabilizer | Stabilizer [ppm] | NCO value [%] | HAZEN Color [APHA] | Viscosity at 25° C. [mPas] | HAZEN Color [APHA] | Viscosity at 25° C. [mPas] | in pressure (pressure test, 12 h, 90° C.) |
| Comparison Example 1 | 10 | — | — | 29.47 | 113 | 37 | 79 | 383 | 6 |

-continued

| | Isocyanate | | | | | Prepolymer | | Pressure test to evaluate the storage stability [bar/d] Rate of increase |
|---|---|---|---|---|---|---|---|---|
| | TMST [ppm] | Stabilizer | Stabilizer [ppm] | NCO value [%] | HAZEN Color [APHA] | Viscosity at 25° C. [mPas] | HAZEN Color [APHA] | Viscosity at 25° C. [mPas] | in pressure (pressure test, 12 h, 90° C.) |
| Comparison Example 2 | 55 | — | — | 29.53 | 349 | 37 | 155 | 383 | 0.1 |
| Comparison Example 3 | 70* | — | — | 29.53 | 560 | 36 | 208 | 365 | 0.1 |
| Example 1 | 10 | IPDC | 200 | 29.67 | 111 | 32 | 102 | 351 | 0.1 |
| Example 2 | 10 | α-CIPA | 100 | 29.65 | 110 | 32 | 83 | 362 | 1 |
| Example 3 | 10 | p-TSME | 100 | 29.48 | 114 | 32 | 80 | 350 | 1 |
| Example 4 | 10 | HCl | 100 | 29.13 | 78 | 42 | 53 | 385 | 1 |
| Example 5 | 10 | SDC | 200 | 29.53 | 87 | 32 | 67 | 349 | 1 |
| Example 6 | 10 | DBP | 200 | 29.02 | 50 | 42 | 63 | 396 | 2 |

*Instead of TMST, trifluoromethanesulfonic acid was employed as the terminator in Comparison Example 3.

Comparison Examples 1 and 2 illustrate the positive influence of the increased amount of TMST terminator on the stability, but at the expense of the color (HAZEN). Comparison Example 3 shows the still more unfavorable influence of the trifluoromethanesulfonic acid terminator on the color (HAZEN). In Examples 1 to 6 which are representative of the present invention, an improved stability was achieved, compared to Comparison Example 1, and the good color level (HAZEN) was also obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of organic isocyanates containing carbodiimide and/or uretonimine groups, comprising:
   (1) partially carbodiimidizing isocyanate groups of an organic isocyanate in the presence of one or more phospholine oxide catalysts,
   (2) subsequently terminating the carbodiimidization reaction by the addition of a silylated acid which corresponds to the formula:

X—[Si(CH$_3$)$_3$]$_n$, wherein:
   X represents the neutral acid radical which is obtained from an n-basic acid having a pKa value of not more than 3 by removal of the acid hydrogen atoms, with the proviso that said n-basic acids exclude hydrogen halide acids,
   and
   n represents an integer from 1 to 3,
   and
   (3) adding a compound selected from the group consisting of non-silylated acids, acid derivatives of non-silylated acids, acid chlorides, sulfonic acid esters and mixtures thereof.

2. The process of claim 1, wherein step (3) the addition of a non-silylated acid, an acid derivative of a non-silylated acid, an acid chloride and/or a sulfonic acid ester is carried out either simultaneously as the addition of the silylated acid, or subsequently to the addition of the silylated acid in a separate step.

3. The process of claim 1, wherein the non-silylated acid, the acid derivatives of non-silylated acid, the acid chloride and/or the sulfonic acid ester are added in amounts of in total between 10 and 1,000 ppm, based on the weight of organic isocyanates containing carbodiimide and/or uretonimine groups.

4. The process of claim 1, wherein the non-silylated acid, the acid derivatives of non-silylated acid, the acid chloride and/or the sulfonic acid ester are added in amounts of in total between 10 and 500 ppm, based on the weight of organic isocyanates containing carbodiimide and/or uretonimine groups.

5. The process of claim 1, wherein the non-silylated acid, the acid derivatives of non-silylated acid, the acid chloride and/or the sulfonic acid ester are added in amounts of in total between 50 and 250 ppm, based on the weight of organic isocyanates containing carbodiimide and/or uretonimine groups.

6. The process of claim 1, wherein the non-silylated acid and/or the acid derivative of the non-silylated acid comprises optionally halogenated, aliphatic and/or cycloaliphatic and/or aromatic, mono-, di- and/or polycarboxylic acids, sulfonic acids, HCl, and/or phosphoric acid, or mono- and/or diesters thereof.

7. The process of claim 6, wherein the non-silylated acid and/or the acid derivative of the non-silylated acid is selected from the group consisting of: acetic acid, adipic acid, cyclohexanedicarboxylic acid, α-chloropropionic acid, benzoic acid, phthalic acid, isophthalic acid, dibutyl phosphate and mixtures thereof.

8. The process of claim 1, wherein the acid chloride comprises one or more acid chlorides derived from optionally halogenated, aliphatic and/or cycloaliphatic and/or aromatic, mono-, di- and/or polycarboxylic acids or sulfonic acids, and carbamic acid chlorides.

9. The process of claim 8, wherein the acid chloride comprises n-butylcarbamic acid chloride.

10. The process of claim 1, wherein the sulfonic acid ester is selected from the group consisting of p-toluenesulfonic acid methyl ester, p-toluenesulfonic acid ethyl ester and mixtures thereof.

* * * * *